United States Patent
Barreca et al.

(10) Patent No.: US 10,131,624 B2
(45) Date of Patent: Nov. 20, 2018

(54) PROCESS FOR THE PREPARATION OF (1S,2R)-MILNACIPRAN

(71) Applicant: QUIMICA SINTETICA, S.A., Barcelona (ES)

(72) Inventors: Giuseppe Barreca, Montevecchia (IT); Bruno Gaetano Romano, Casatenovo (IT)

(73) Assignee: QUIMICA SINTETICA, S.A., Barcelona (ES)

( * ) Notice: Subject to any disclaimer, the term of this patent is extended or adjusted under 35 U.S.C. 154(b) by 29 days.

(21) Appl. No.: 15/523,560

(22) PCT Filed: Nov. 3, 2015

(86) PCT No.: PCT/EP2015/075513
§ 371 (c)(1),
(2) Date: May 1, 2017

(87) PCT Pub. No.: WO2016/071303
PCT Pub. Date: May 12, 2016

(65) Prior Publication Data
US 2018/0273468 A1    Sep. 27, 2018

(30) Foreign Application Priority Data
Nov. 4, 2014 (IT) .............................. MI2014A1883

(51) Int. Cl.
*C07C 233/57* (2006.01)
*C07C 231/06* (2006.01)
*C07C 231/12* (2006.01)
*C07C 231/02* (2006.01)

(52) U.S. Cl.
CPC .......... *C07C 231/12* (2013.01); *C07C 231/02* (2013.01); *C07B 2200/07* (2013.01); *C07C 2601/02* (2017.05)

(58) Field of Classification Search
CPC ... C07C 231/18; C07C 233/58; C07C 237/20; C07C 237/24; C07C 2601/02
See application file for complete search history.

(56) References Cited

FOREIGN PATENT DOCUMENTS

| EP | 0200638 A1 | 4/1986 |
| EP | 0377381 B1 | 4/1992 |
| EP | 1845084 A1 | 10/2007 |
| EP | 2123628 B1 | 6/2012 |
| EP | 2391599 B1 | 4/2014 |
| WO | 2010086394 A1 | 8/2010 |
| WO | 2012059933 A1 | 5/2012 |
| WO | 2014009767 A1 | 1/2014 |

OTHER PUBLICATIONS

Green, Protective Groups in Organic Synthesis, (John Wiley & Sons), p. 565 (1999).
Bonnard, et al., Journal of Chromatography, 318:398-403 (1985).
Shuto, et al., Tetrahedron Letters, vol. 37, No. 5, pp. 641-644 (1996).
International Search Report for PCT/EP2015/075513 dated Jan. 27, 2016.

*Primary Examiner* — Jafar F Parsa
(74) *Attorney, Agent, or Firm* — Abelman, Frayne & Schwab

(57) ABSTRACT

The invention relates to a process for the preparation of Levomilnacipran or salts thereof, compounds useful in the treatment of depression, with high yield.

11 Claims, No Drawings

PROCESS FOR THE PREPARATION OF (1S,2R)-MILNACIPRAN

RELATED APPLICATIONS

This application is a national phase of International Application No. PCT/EP2015/075513 filed Nov. 3, 2015, and claims priority from Italian Patent Application No. MI2014A001883 filed Nov. 4, 2014, both incorporated by reference in their entirety.

FIELD OF THE INVENTION

The present invention relates to an industrially applicable and advantageous process for the preparation of (1S,2R)-Milnacipran (generally known as Levomilnacipran) or a salt thereof.

STATE OF THE ART (1S,2R)-2-aminomethyl)-N,N-diethyl-1-phenylcyclopropanecarboxamide, also known as Levomilnacipran, is an active principle useful in the treatment of depression for its ability to act as an inhibitor of the reuptake of serotonin-norepinefphrine. Said compound is characterized by the following structural formula:

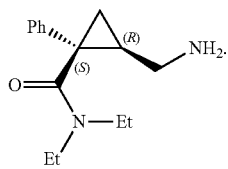

The preparation of Milnacipran (i.e. the racemic form of Levomilnacipran) or salts thereof has been widely described in the literature. For example, European patent EP 0377381 B1 describes a process for the preparation of an intermediate useful in the synthesis of Milnacipran, which provides for the transformation of the racemic lactone (±-A), into the corresponding alcohol (±-D), which, upon activation as chloride (±-F), is converted to the corresponding amide (±-C) by treatment with potassium phthalimide:

Alternatively, as described in European Patent EP 200638 B1, the racemic lactone (±-A) may be treated with potassium phthalimide to obtain the acid (±-B) which is then converted into amide (±-C) by treatment with thionyl chloride followed by diethyl amine.

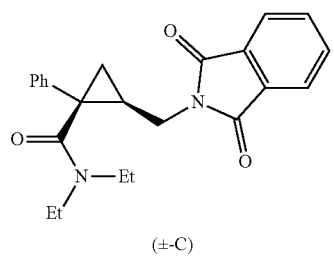

Alcohol (±-D) can also be converted into amide (±-C) using the procedure described in European Patent EP 1845084 B1, i.e. by treatment with methanesulfonic acid in the presence of triethyl orthoformate and subsequent conversion of the salt (±-E) into the desired product by treatment with potassium phthalimide.

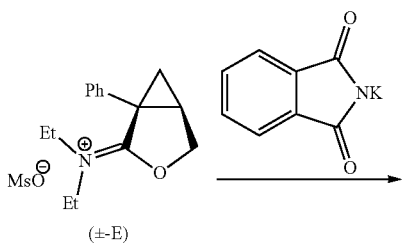

(±-E)

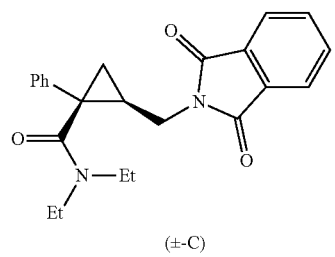

(±-C)

A first method for obtaining enantiomerically enriched Levomilnacipran, by separation of the racemic mixture by chromatography on a chiral column, has been described in *J. Chromatogr.* 1985, 318, 398-403.

European Patent EP 2123628 B1 and international application WO 2012/059933 A1 describe a process for the preparation of Levomilnacipran by means of an optical resolution of Milnacipran by treatment with a derivative of tartaric acid and with mandelic acid, respectively.

One disadvantage associated with these methods arises from the use of fractional crystallization or a chromatography on a chiral column to separate the two enantiomers of Milnacipran. In fact, the first process leads to a drastic decrease in the overall yield, because at least 50% of the product must be discarded, while the second one is barely or not industrially applicable.

Some synthetic approaches have been developed subsequently to prepare the enantiomerically enriched form of Milnacipran, as described for example in *Tetrahedron Letters* 1996, 37, 641-644.

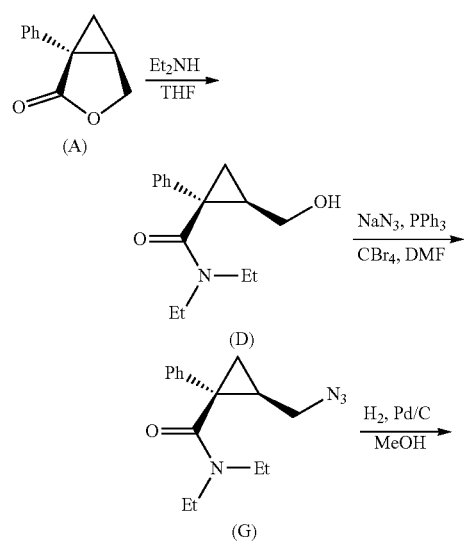

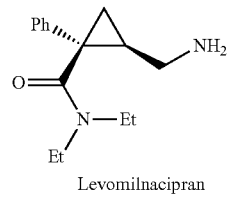

Levomilnacipran

However, these synthetic routes provide for the use of sodium azide, a reagent whose use on an industrial scale should be limited because of its toxicity and the fact that it can give rise to products and by-products which decompose with explosive course.

A further synthesis route for the preparation of Levomilnacipran has been described in patent EP 2391599 B1. This route provides for the use of the same synthetic scheme described in patent EP 200638 B1 previously reported, using an enantiomerically enriched form of lactone (A) as starting compound, so as to obtain Levomilnacipran instead of Milnacipran.

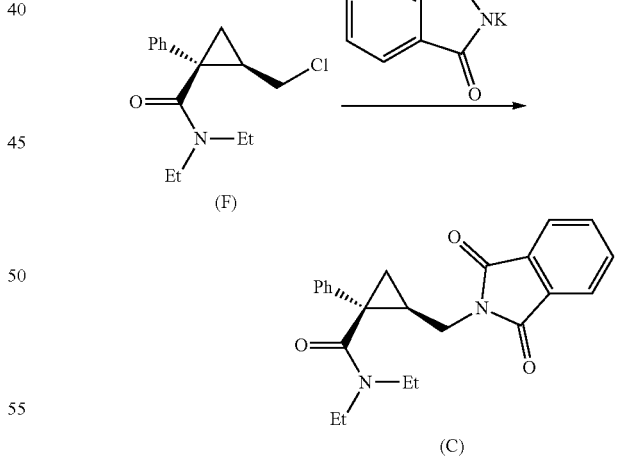

A latter synthetic approach, described in international application WO 2014/009767 A1, provides for the preparation of Levomilnacipran by reaction of enantiomerically enriched alcohol (D) with sodium azide in the presence of diethyl azodicarboxylate followed by reduction of the thus obtained azide by treatment with triphenylphosphine. This reaction involves the use of hydrazoic acid (and not sodium azide as erroneously stated in the application), and should therefore be avoided on an industrial scale because of the high toxicity and explosiveness of this compound, as described in *Breterick's Handbook of reactive chemical hazards*, Elsevier 7th edition, pages 1669-1670.

The object of this invention is to provide a method for the synthesis of Levomilnacipran, which is realized with high yields provides the desired products with a degree of purity suitable for pharmaceutical use.

SUMMARY OF THE INVENTION

These objects are achieved with the present invention that, in a first aspect thereof, relates to a process for the preparation of (1S,2R)-Milnacipran that comprises the following steps:

a) directly converting the enantiomerically enriched form of alcohol (D) into the enantiomerically enriched form of the phthalimido derivative (C) by treatment with phthalimide in the presence of a trialkyl- or triarylphosphine and of a dialkyl azodicarboxylate:

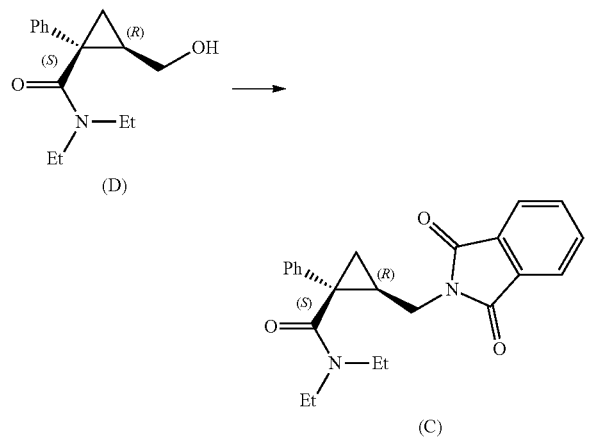

wherein the amount of phthalimide is comprised between 1 and 1.3 equivalents with respect to the molar amount of alcohol (D) used, and the amounts of both the phosphine and the azodicarboxylate are comprised, independently from each other, between 1 and 1.5 equivalents with respect to the molar amount of alcohol (D) used;

b) deblocking the enantiomerically enriched form of the phthalimido derivative (C) to obtain Levomilnacipran:

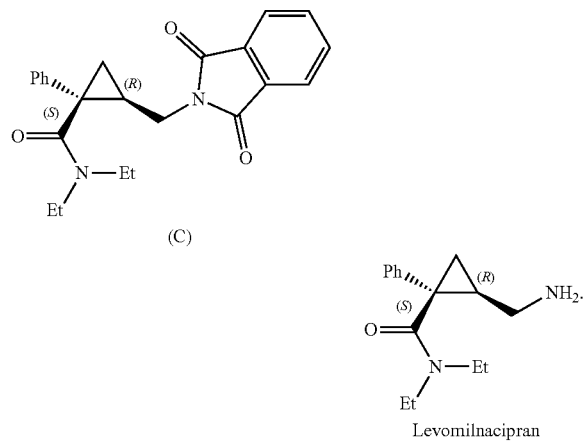

In this first aspect, the invention can comprise an additional optional step b') consisting in the treatment with an inorganic base in order to increase the yield in the isolation of Levomilnacipran.

In a second aspect thereof, the invention consists in the transformation of the Levomilnacipran thus obtained into a pharmaceutically acceptable salt thereof, with a process step c) that consists in transforming the Levomilnacipran, obtained according to the sequences of steps a)-b) or a)-b') described above, into a salt by treatment with a pharmaceutically acceptable acid (HY):

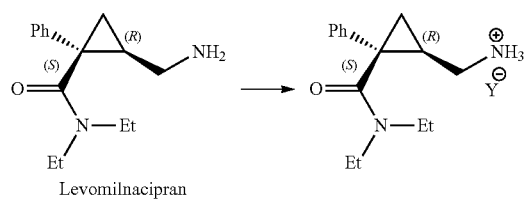

wherein $Y^{\ominus}$ is the conjugate base of said acid.

DETAILED DESCRIPTION OF THE INVENTION

All terms used in this application, unless otherwise stated, are to be understood in their ordinary meaning as known in the field. More detailed specifications for certain terms used in this application are listed below and should be applied uniformly to the entire specification and claims, unless otherwise indicated.

The enantiomeric purity is usually expressed as "enantiomeric excess" or ee, which is defined, for example for the (S) enantiomer, as:

$$ee=[(S-R)/(R+S)]\times 100$$

where S and R are respective amounts of the two enantiomers (S) and (R) (as determined for example by HPLC or GC on chiral stationary phase).

The term "racemic mixture" and derived terms relate to a sample of a chiral compound that contains equal amounts of the two optical isomers (+) and (−).

The terms "enantiomerically enriched form" or "enantiomerically enriched mixture" as used in this application indicate mixtures in which one of the two enantiomers is present in excess with respect to the other.

The term "(S) or (R) enantiomer in enantiomerically pure form" refers to a sample of a chiral compound whose enantiomeric purity is at least 99%, even more preferably 99.5%.

The symbol ⋯⋯ (dashed bond) present in some of the formulas of the specification and claims indicates that the substituent is directed below the plane of the sheet.

The symbol ━━ (wedge bond) present in some of the formulas of the specification and claims indicates that the substituent is directed above the plane of the sheet.

In general, the nomenclature used in this application is based on AUTONOM® v. 4.0, a Beilstein Institute computerized system for assigning IUPAC systematic nomenclature. In case of a discrepancy between a sketched structure and the name assigned to this structure, the formula specified should be considered correct. In addition, if the stereochemistry of a structure or a portion of the structure is not indicated, for example with a wedge or dashed bond, such structure or portion thereof should be understood as encompassing all stereoisomers.

According to its most general aspect the present invention relates to the preparation of Levomilnacipran or salts thereof.

The first step of the process of the invention, a), provides for the direct conversion of the enantiomerically enriched form of alcohol (D) into the enantiomerically enriched form of phthalimido derivative (C) by treatment with phthalimide in an amount between 1 and 1.3 equivalents, preferably between 1 and 1.05 equivalents, with respect to the molar amount of the alcohol (D) used, in the presence of a trialkyl- or triarylphosphine and a dialkyl azodicarboxylate. This reaction, known as the Mitsunobu reaction, is normally carried out by treatment of an alcohol with a dialkyl azodicarboxylate (for example diethyl azodicarboxylate or preferably diisopropyl azodicarboxylate) and a nucleophile (the phthalimide) in the presence of a trialkyl- or triarylphosphine (for example, tri-normal-butylphosphine or preferably triphenylphosphine) in an aprotic polar solvent such as a chlorinated solvent (for example dichloromethane) or an ether (for example tetrahydrofuran, 1,4-dioxane or preferably 2-methyltetrahydrofuran), at a temperature between −30 and 30° C., preferably between 0 and 5° C.

The amounts of both phosphine and azodicarboxylate are comprised, independently from each other, between 1 and 1.5 equivalents with respect to the molar amount of alcohol (D) used; preferably these amounts are respectively 1.2 and 1.1 equivalents.

The enantiomerically enriched form of alcohol (D) optionally purified and isolated can be prepared in a step a') preliminary and preparatory to the process of the invention according to techniques known in the field, for example as described in European patent EP 2391599 B1, that is, by treatment of an enantiomerically enriched form of lactone (A) with diethylamine in the presence of a Lewis acid, preferably aluminum trichloride.

The following step b) consists in deblocking the enantiomerically enriched form of phthalimido derivative (C) in order to obtain Levomilnacipran according to one of the procedures described in Theodora W. Green, *Protective Groups in Organic Synthesis*, John Wiley & Sons (1999), page 565, which are incorporated by reference in the present application. This step can be carried out preferably by treatment with hydrazine, an alkylamine (preferably a 40% w/w aqueous solution of methylamine) or a hydroxyalkylamine, for example ethanolamine in an aprotic polar solvent, such as an ether (for example tetrahydrofuran, 1,4-dioxane or preferably 2-methyltetrahydrofuran), at a temperature between 0 and 50° C., preferably between 20 and 30° C.

The amount of hydrazine, alkylamine or hydroxyalkylamine can vary in a very wide range; preferably, said amount can vary between 2 and 25 equivalents with respect to the molar quantity of phthalimido derivative (C) used; even more preferably, said amount can vary between 5 and 15 equivalents with respect to the molar quantity of phthalimido derivative (C) used, for example 11 equivalents.

In a possible variation of this first aspect of the invention, subsequently to step b) an additional step b') is conducted that includes a treatment with an inorganic base, for example a carbonate (preferably an aqueous solution of $Na_2CO_3$, $Li_2CO_3$ or $K_2CO_3$) or a hydroxide (preferably an aqueous solution of LiOH, KOH or NaOH). This step has the aim of increasing the yield of the phthalimide deblocking reaction and prevents that the phthalimido derivative (C) forms again during the Levomilnacipran isolation steps.

In its second aspect, the invention includes the conversion of Levomilnacipran obtained as described above, with or without the implementation of the optional step b'), into a pharmaceutically acceptable salt thereof, preferably its hydrochloride. This step c) is achieved by treatment with a pharmaceutically acceptable protic acid HY, in the preferred case through the use of an aqueous solution of hydrochloric acid or a solution of hydrogen chloride in an organic solvent (for example an alcohol, preferably methanol).

According to one preferred embodiment, all of the above steps of the process of the invention are carried out without isolation of the intermediate compounds.

When Levomilnacipran, or any other compound described in the present application, is obtained with a degree of chemical purity not suitable for inclusion in a medicament, the process includes an additional purification step, for example by chromatography or crystallization, optionally after formation of a compound of addition, such as a salt or co-crystal, or by washing with an organic solvent or an aqueous solution, optionally after changing the pH.

The invention will be further illustrated by the following examples.

In the following examples, monitoring of progress and completion of the reactions described was performed by HPLC.

HPLC Method
Column: Symmetry C18 250×4.6 mm 5 µm or equivalent
Flow rate: 1.0 mL/min
Injection volume: 10 µL
Wavelength: 210 nm
Column T: 35° C.
Mobile phase:
Phase A: 0.1% $H_3PO_4$ aqueous solution
Phase B: acetonitrile
Gradient:

| Flow rate: (mL/min) | Time | Phase A (%) | Phase B (%) |
|---|---|---|---|
| 1 | 0 | 90 | 10 |
| 1 | 20 | 50 | 50 |
| 1 | 35 | 10 | 90 |
| 1 | 40 | 10 | 90 |
| 1 | 41 | 90 | 10 |

Example 1

Synthesis of (1S,2R)—N,N-diethyl-2-(hydroxymethyl)-1-phenylcyclopropane-carboxamide (D)

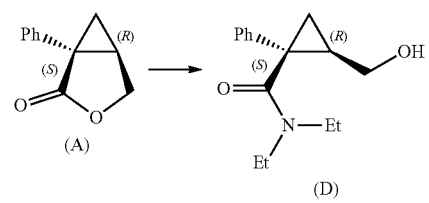

Diethylamine (1.56 g, 21.3 mmol) is added dropwise to a suspension of aluminum trichloride (1.38 g, 10.4 mmol) in toluene (9.6 mL), cooled to 0° C. under magnetic stirring and in nitrogen atmosphere, checking that the internal temperature of the system does not exceed 15° C. The obtained solution is maintained at 25° C. for about 30 minutes, then a toluene (2 mL) solution of lactone A (1.50 g, 8.6 mmol) is slowly added. The mixture is maintained under magnetic stirring at 25° C. up to complete conversion (about 2 hours), then poured into water (7.2 mL) previously cooled to 5° C., checking that the internal temperature does not exceed 25° C. The obtained phases are separated and the aqueous phase extracted with toluene. The organic phase is filtered on a panel of activated carbon and celite, and concentrated at reduced pressure until a residue of 2.50 g (containing about 2.10 g of the desired product) is obtained, which is used in the next step without any further purification.

Example 2

Synthesis of (1S,2R)-2-((1,3-dioxoisoindolin-2-yl)methyl)-N,N-diethyl-1-phenyl-cyclopropanecarboxamide (C)

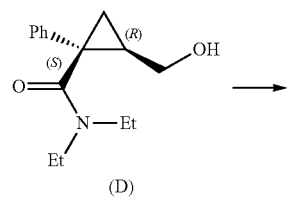

(D)

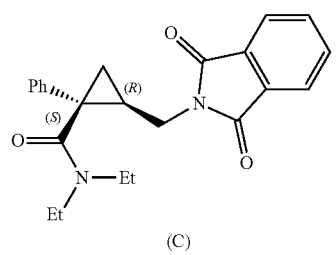

(C)

2-methyltetrahydrofuran (9 mL) is added to the residue prepared as described in Example 1 (2.50 g, 8.6 mmol) under magnetic stirring and in an inert nitrogen atmosphere until a solution is obtained, and then phthalimide powder (1.30 g, 8.8 mmol) and triphenylphosphine (2.60 g, 9.9 mmol) are added. The resulting suspension, cooled to −15° C., is slowly added with a solution of diisopropyl azodicarboxylate (DIAD) (1.80 g, 8.9 mmol) in 2-methyltetrahydrofuran (4.5 mL). At the end of the addition, the temperature of the mixture is raised up to 5° C. and kept under the same conditions up to complete conversion (about 2 hours). The mixture temperature is brought to 25° C., and then water is added (4.5 mL) and the phases are separated. The organic phase is used in the next step without any further purification.

Example 3

Synthesis of hydrochloride of (1S,2R)-2-(aminomethyl)-N,N-diethyl-1-phenylcyclopropanecarboxamide (Levomilnacipran hydrochloride)

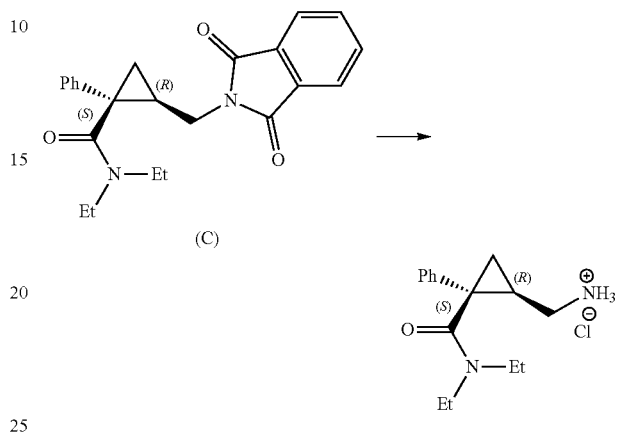

A 40% w/w methylamine aqueous solution (7.50 g, 96.6 mmol) is added to the solution prepared as described in Example 2 (18.00 g of solution containing 8.6 mmol of C) under magnetic stirring and in nitrogen atmosphere. The resulting mixture is maintained under magnetic stirring at 25° C. up to complete conversion (about 3 hours), and then a 30% w/w sodium hydroxide aqueous solution (4.50 g, 33.7 mmol) is added and the mixture is left under stirring for further 30 minutes. The phases are separated and the aqueous phase is extracted with 2-methyltetrahydrofuran (4.5 mL). The combined organic phases are concentrated to reduce the volume to about 10 mL, then water (6 mL), 2-methyltetrahydrofuran (20 mL) and a 37% w/w hydrochloric acid aqueous solution (1.30 g, 12.8 mmol) are added up to a pH of about 1 and checking that the internal temperature of the system does not exceed 30° C. At the end of the addition, the phases are separated and the organic phase is extracted twice with water (4.5 mL) and a 37% w/w hydrochloric acid aqueous solution (0.60 g, 5.9 mmol). The combined aqueous phases are added with 2-methyltetrahydrofuran (9 mL) and a 30% w/w sodium hydroxide aqueous solution (3.50 g, 26.0 mmol), checking that the temperature of the system does not exceed 30° C. The phases are separated and the aqueous phase is extracted three times with 2-methyltetrahydrofuran (4.5 mL). The combined organic phases are concentrated under reduced pressure until a residue is obtained. The obtained oil is solubilized in isopropyl acetate (4.5 mL) and maintained under magnetic stirring until obtaining a solution that is filtered on a panel of activated carbon and celite. A 15% w/w hydrochloric acid solution (2.10 g, 8.6 mmol) in methanol is added to the filtrate, kept at 30° C., until a pH between 1 and 2 is obtained. The solution is heated to reflux at atmospheric pressure to remove the methanol until the internal temperature is in the 84 to 85° C. range, while adding isopropyl acetate in order to maintain the volume of the mixture constant. The solution is left to cool to a temperature between 15 and 20° C., then the suspension is filtered and the solid is washed with isopropyl acetate. The product is dried at 40° C. at reduced pressure until a constant weight is reached. 2.30 g of Levomilnacipran hydrochloride are obtained with a yield of 94% with respect to the amount of compound (A) used.

Example 4

Synthesis of (1S,5R)-1-phenyl-3-oxabicyclo[3.1.0]hexan-2-one (A)

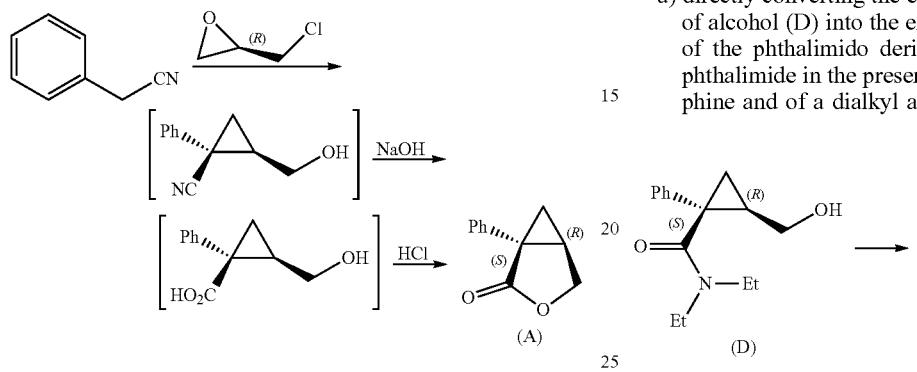

Phenylacetonitrile (7.00 g, 59.6 mmol) is added to a solution of (R)-epichlorohydrin (2.80 g, 30.3 mmol) in toluene (28 mL). Sodium amide (2.80 g, 71.7 mmol) is added portionwise to the obtained solution, cooled to −40° C., checking the evolution of gas and that the internal temperature of the system does not exceed −30° C. When the reaction is complete (about 30 minutes after the last addition) the mixture is slowly poured into water checking that the system temperature does not exceed 20° C. The obtained phases are separated and the organic phase is concentrated at reduced pressure until an oil is obtained. A 30% w/w sodium hydroxide aqueous solution (12.60 g, 94.4 mmol) is added to the residue under magnetic stirring, then the mixture is heated to reflux up to complete conversion (about 3 hours). The mixture is cooled to 25° C. and is poured into a mixture of water (14 mL) and toluene (20 mL). The phases are separated, washing the aqueous phase with toluene. Toluene (22 mL) and a 36% w/w hydrochloric acid aqueous solution (14.00 g, 138.3 mmol) is added to the obtained mixture until a pH below 1 is obtained. The mixture is heated up to 65° C. under magnetic stirring and maintained under the same conditions up to complete conversion (about 2 hours), then the phases are separated. The organic phase is washed with water and then, after cooling to 30° C., it is further washed with a 5% w/w sodium bicarbonate aqueous solution and with water. The organic phase is concentrated under reduced pressure until a residue is left which is taken-up with isopropanol by heating to reflux until a solution is obtained. The mixture is cooled to 5° C. up to complete precipitation, then the solid is filtered and washed with isopropanol. 2.70 g of (A) are obtained with a yield of 51% with respect to the amount of (R)-epichlorohydrin used.

Comments to Examples 1 to 3

The procedure described in examples 1 to 3, subject of steps a')-c) described above, allows obtaining of Levomilnacipran hydrochloride with a 94% isolated yield over the amount of compound (A) used. This yield and consequently the method which allows to obtain it must be considered of particular significance when compared with the procedures described in the documents of the prior art, which allow a recovery of Levomilnacipran hydrochloride with a 66% yield (EP 2391599 B1) or of Milnacipran with a 81% yield (EP 1845084 B1).

The invention claimed is:

1. A Process for the preparation of Levomilnacipran ((1S,2R)-2-(aminomethyl)-N,N-diethyl-1-phenylcyclopropanecarboxamide) comprising the following steps:
    a) directly converting the enantiomerically enriched form of alcohol (D) into the enantiomerically enriched form of the phthalimido derivative (C) by treatment with phthalimide in the presence of a trialkyl or triarylphosphine and of a dialkyl azodicarboxylate:

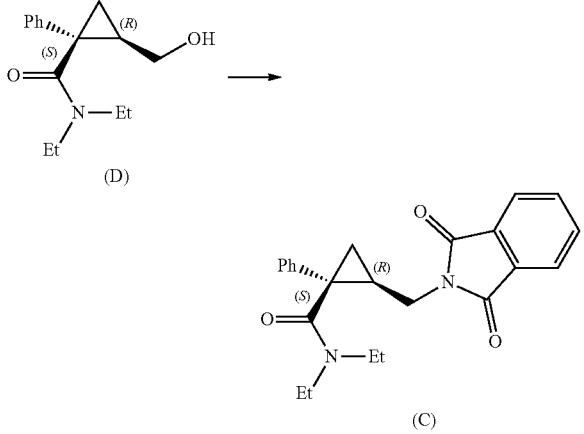

wherein the amount of phthalimide is comprised between 1 and 1.3 equivalents with respect to the molar amount of alcohol (D) used, and the amounts of both the phosphine and the azodicarboxylate are comprised, independently from each other, between 1 and 1.5 equivalents with respect to the molar amount of alcohol (D) used;
    b) deblocking the enantiomerically enriched form of the phthalimido derivative (C) to obtain Levomilnacipran:

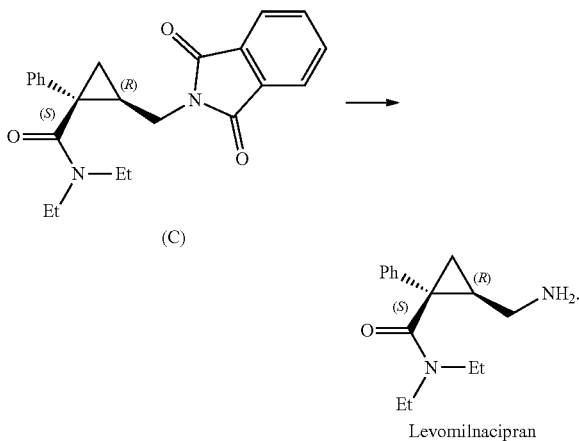

2. The process according to claim 1, comprising an additional step b') carried out after step b), consisting of treating said Levomilnacipran with an inorganic base.

3. The process according to claim 1, wherein in step a) the amount of phthalimide comprises between 1 and 1.05 equivalents with respect to the molar amount of alcohol (D) used.

4. The process according to claim 1, wherein step a) is carried out in an aprotic polar solvent selected from the group consisting of a chlorinated solvents and an ether.

5. The process according to claim 1, wherein step b) is carried out by treatment with a compound selected from the group consisting of hydrazine, an alkylamine and a hydroxyalkylamine.

6. The process according to claim 5, wherein the amount of hydrazine, alkylamine or hydroxyalkylamine comprises between 2 and 25 equivalents with respect to the molar amount of the phthalimido derivative (C).

7. The process according to claim 2, wherein the inorganic base used in step b') is selected from the group consisting of a carbonates and a hydroxides.

8. The process according to claim 1, further comprising converting said Levomilnacipran into a pharmaceutically acceptable salt thereof by treating said Levomilnacipran with a protic acid HY, according to step c):

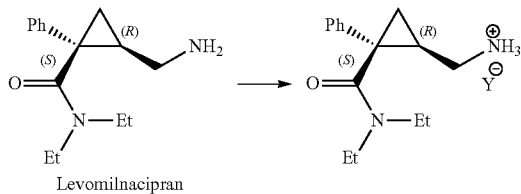

Levomilnacipran wherein $Y^\ominus$ is the conjugate base of said acid.

9. The process according to claim 1, wherein the enantiomerically enriched form of alcohol (D) is prepared in a step a') prior to step a), by treating the enantiomerically enriched form of lactone (A) with diethylamine in the presence of a Lewis acid:

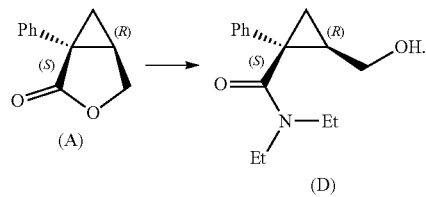

10. The process according to claim 9, wherein steps a')-c) of the process are carried out without isolation of the intermediate compounds.

11. The process according to claim 2, further comprising converting said Levomilnacipran into a pharmaceutically acceptable salt by treating said Levomilnacipran with a protic acid HY according to step (c):

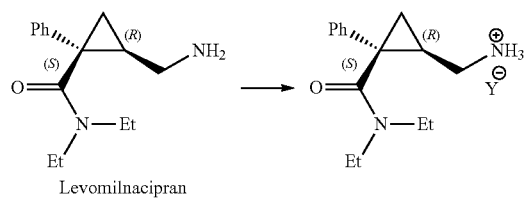

Levomilnacipran wherein $Y^\ominus$ is the conjugate base of said protic acid.

* * * * *